United States Patent [19]
Andersson

[11] Patent Number: 4,968,309
[45] Date of Patent: Nov. 6, 1990

[54] CONNECTION PREFERABLY FOR MEDICAL USE

[76] Inventor: Ingvar Andersson, SkolgÅrdsvägen 3, S-182 74 FiskebÄckskil, Sweden

[21] Appl. No.: 305,725
[22] PCT Filed: Aug. 5, 1987
[86] PCT No.: PCT/SE87/00349
§ 371 Date: Jan. 30, 1989
§ 102(e) Date: Jan. 30, 1989
[87] PCT Pub. No.: WO88/00839
PCT Pub. Date: Feb. 11, 1988
[51] Int. Cl.$^5$ ............................................. A61M 25/00
[52] U.S. Cl. ..................... 604/283; 604/83; 604/905
[58] Field of Search ................ 604/283, 83, 905, 411, 604/29, 30

[56] References Cited
U.S. PATENT DOCUMENTS

| | | | |
|---|---|---|---|
| 4,262,671 | 4/1981 | Kersten | 604/411 X |
| 4,506,691 | 3/1985 | Tseo | 604/83 X |
| 4,576,199 | 3/1986 | Svensson et al. | 604/905 X |
| 4,617,012 | 10/1986 | Vaillancourt | 604/29 |

FOREIGN PATENT DOCUMENTS 2387044 4/1978 France .
81/00053 1/1981 PCT Int'l Appl. .

Primary Examiner—John D. Yasko
Attorney, Agent, or Firm—Jeffers Hoffman & Niewyk

[57] ABSTRACT

A connection including two attachable halves having respective unions, and a device movably supported within a first half and enclosed within a space defined by the halves. The device is movable to open flow channels between the unions when the halves are attached to one another, and to block the flow channels at least when the halves are separated from one another. The space communicates with or constitutes a part of the flow channels when the device is in one position, or when the halves are in a relative position separate from the connection position. The space forms a closed chamber separated from the flow channels when the device is in another position, or when the halves are in an attached position. A fluid, preferably with disinfectant properties, may be introduced into and removed from the space through penetrable membranes in walls of the halves.

9 Claims, 12 Drawing Sheets

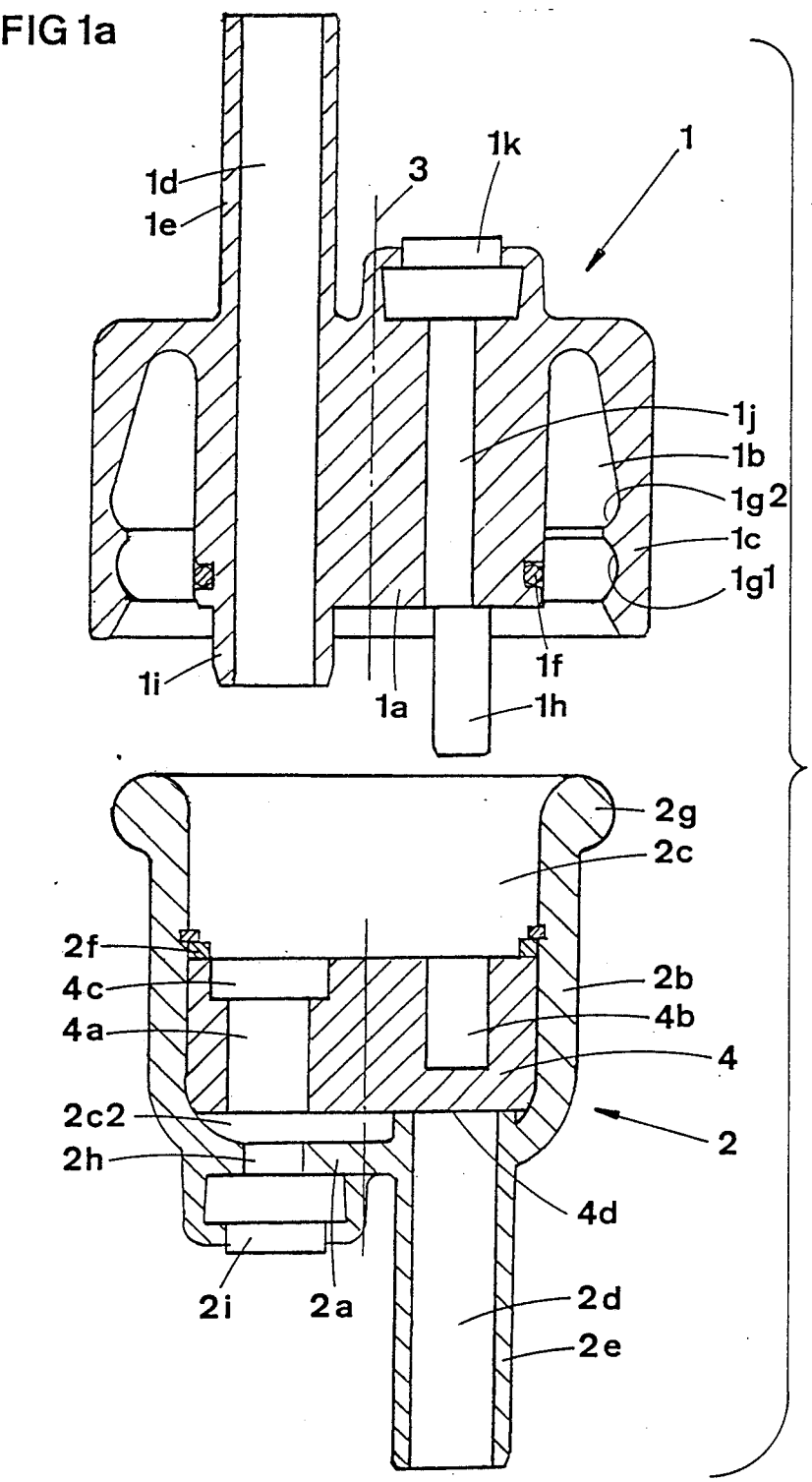

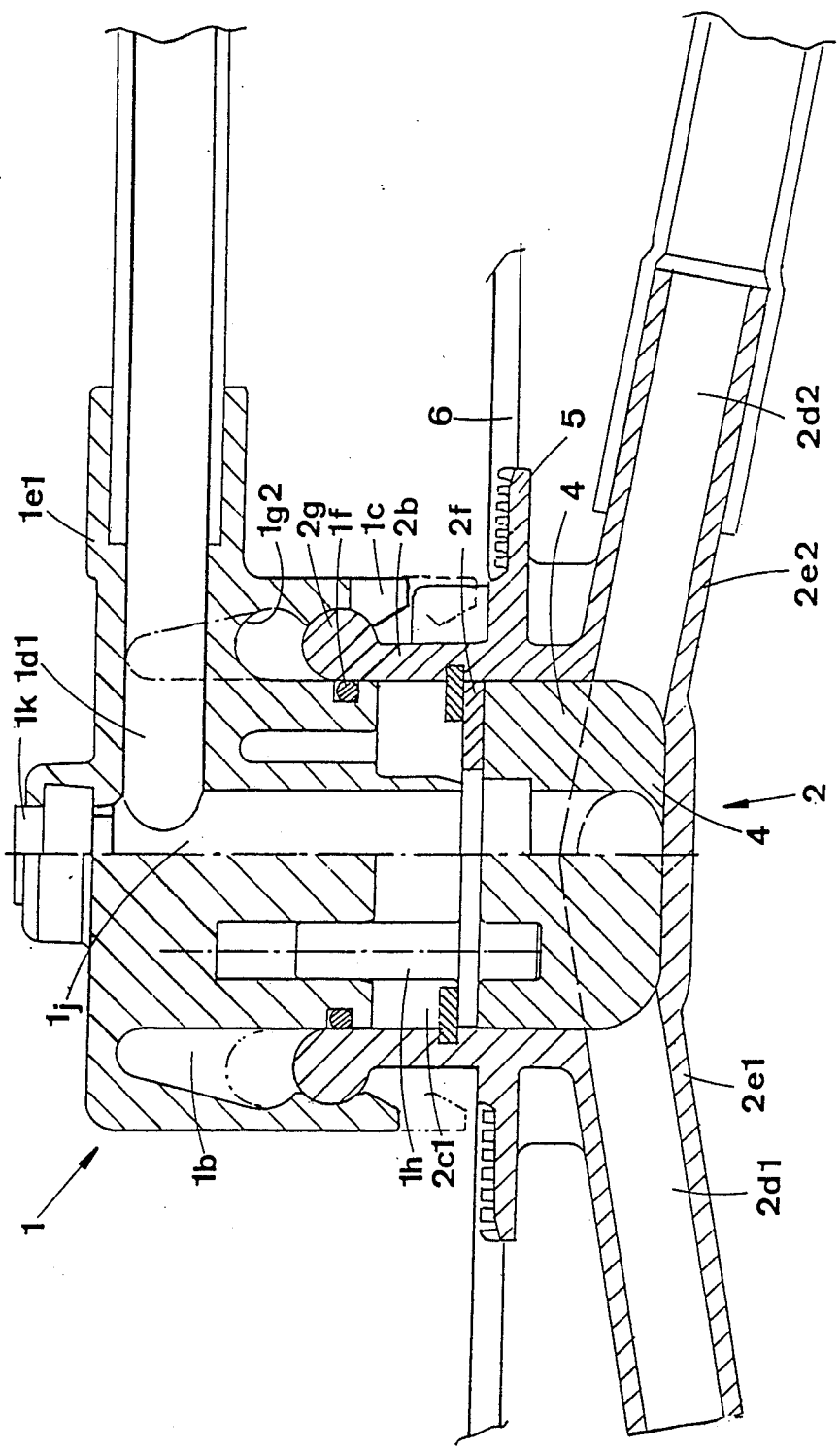

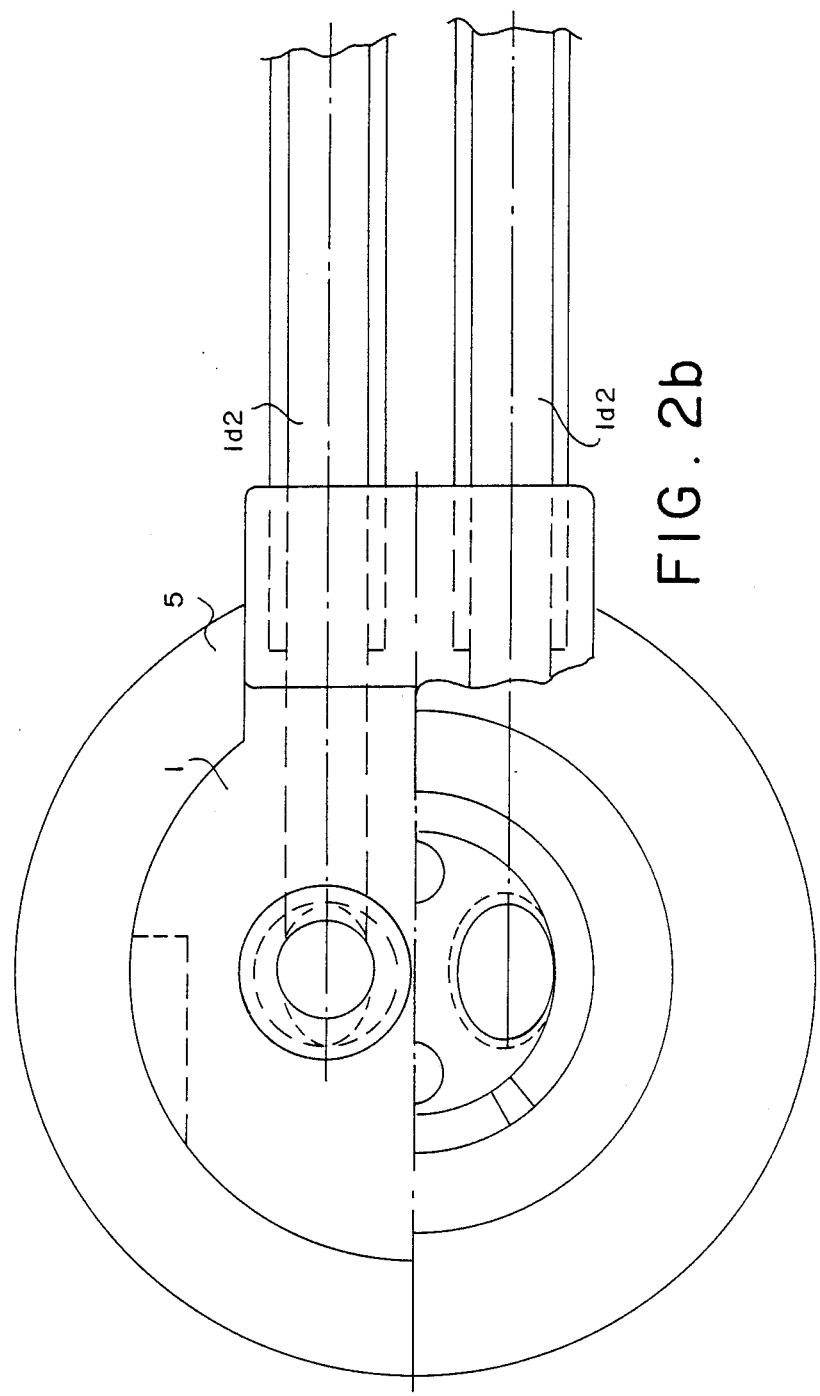

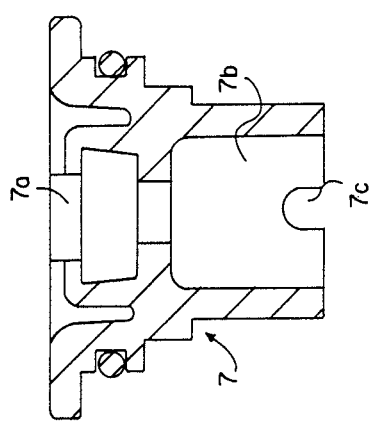
FIG. 3f2
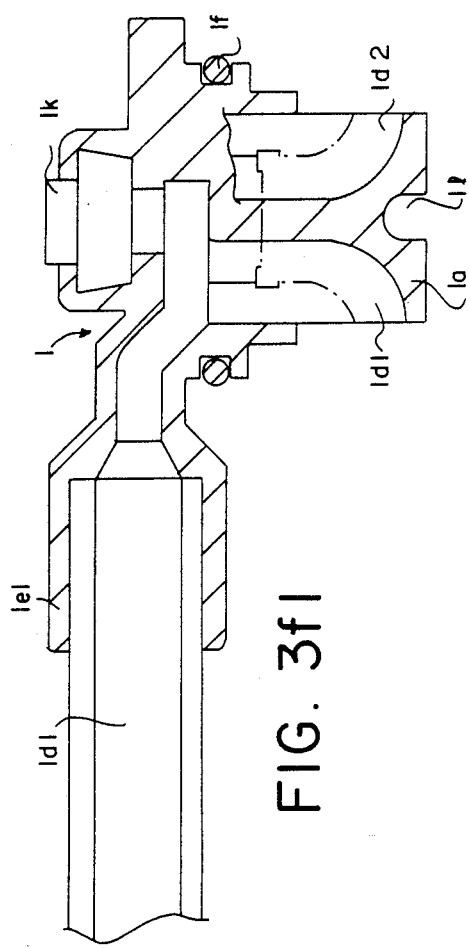
FIG. 3f1
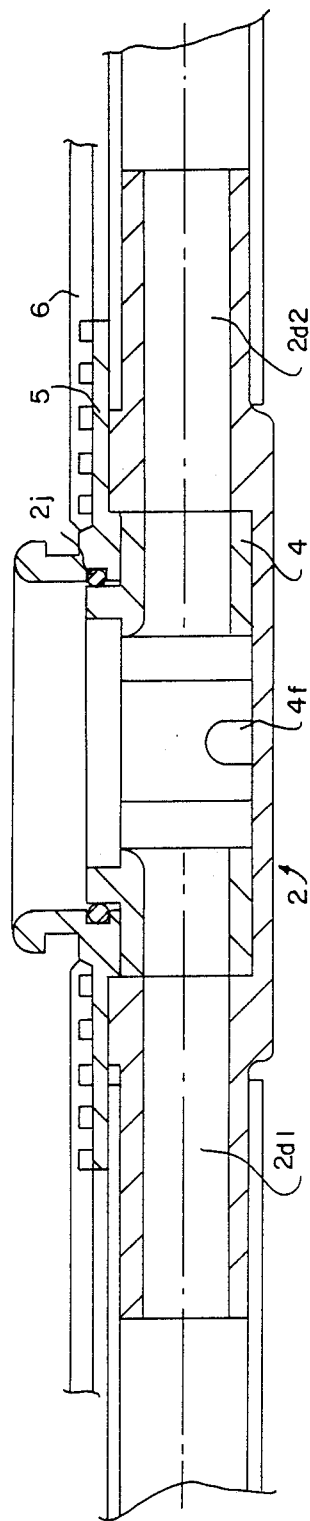
FIG. 3a

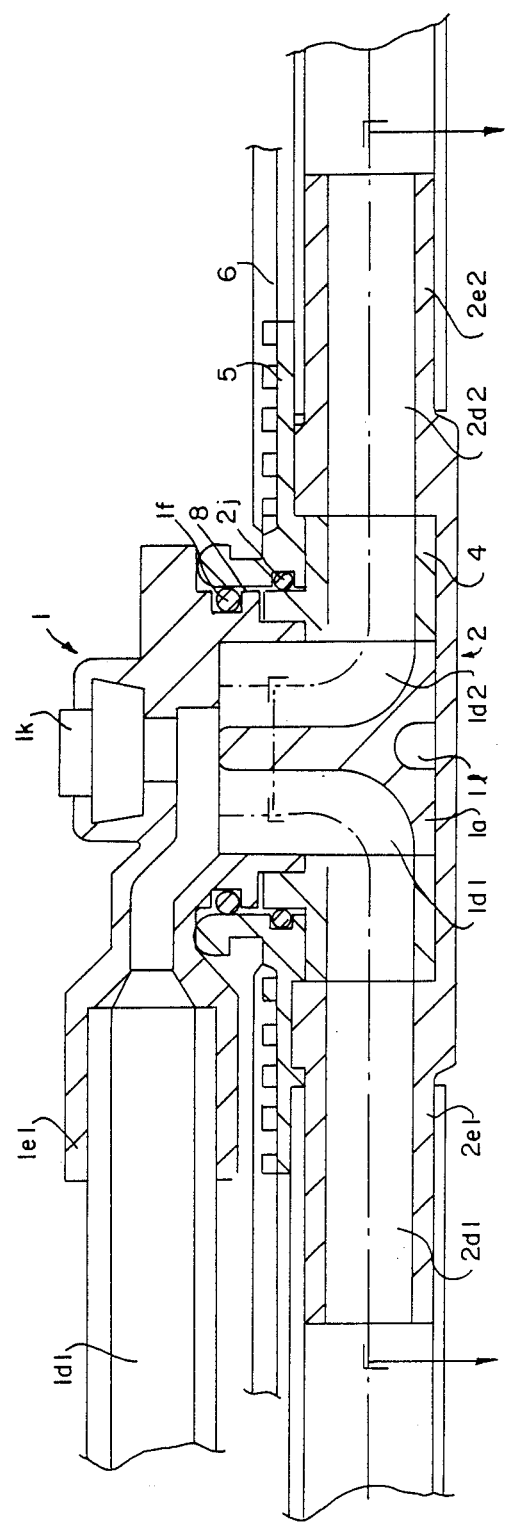

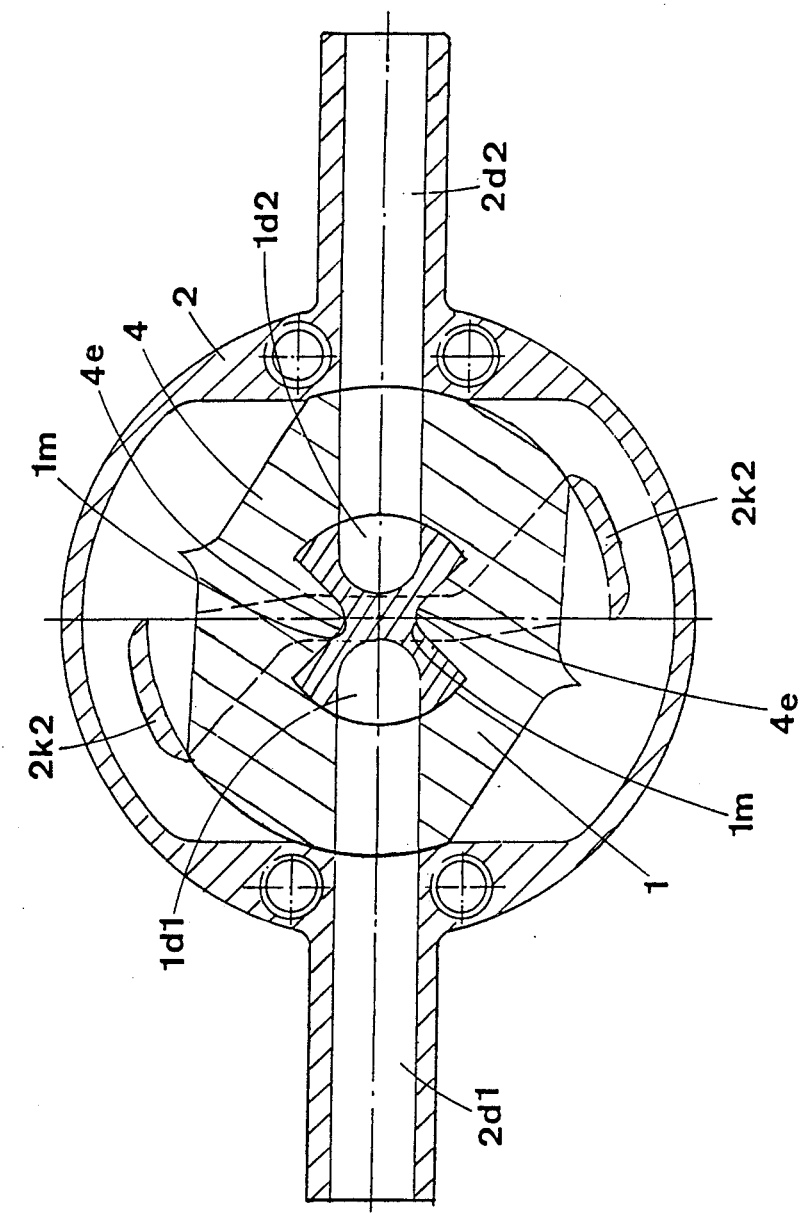

CONNECTION PREFERABLY FOR MEDICAL USE

The present invention relates to a connection, especially for medical applications, comprising two connection halves capable of being attached to one another and separated from one another, each having at least one union, and a device supported in the first and/or in the second connection half in such a way that it is free to move, and so arranged, when in distinct positions relative to the aforementioned connection halves, as to open flow channels between the unions when the halves are attached to one another, and to block the flow channels at least when the halves are separated from one another.

A problem which has long been familiar, in particular in the medical field, is how to produce simple and manageable flow channels which are also secure against external infection and which can be separated from one another and connected together This is particularly applicable to one half of a separable flow channel which for some reason cannot be replaced, for example when draining fluid from a wound from an area of the body which has been the subject of surgical operation, or when one half of the flow channel has been inserted partially beneath the skin by surgery with connections to veins or arteries, for instance.

This problem has been solved in many cases by the expedient of providing the flow channels with self-sealing membranes made of an elastic material capable of being penetrated by a cannula, for example. In certain cases flow channels fitted with membranes are inserted beneath the skin by surgery. In this way the skin has also functioned as a kind of membrane.

This previously disclosed technique exhibits clear limitations. In order to achieve a self-sealing effect both in the skin and in the membrane, which is important from the point of view of preventing infection, the external area of the cannula must be severely restricted. This also means that the flow area inside the cannula is restricted, which in turn causes numerous problems In the case of blood transfusions or blood purification (dialysis), for example, the internal blood pressure of the body is not able to force out sufficiently large quantities of blood per unit of time. The use of auxiliary equipment in the form of blood pumps then becomes necessary. Such a forced flow through narrow passageways and around sharp corners, such as are constituted by a cannula tube, and the mangling of the blood caused by a blood pump, cause the destruction of blood cells, resulting in changes in the chemical properties of the blood.

The object of the present invention is to make available a separable and reconnectable, disinfectable connection in which the aforementioned problem in respect of the restriction of the flow area and the associated pressure drop has been overcome so that the normal blood pressure of the body is sufficient in most cases for blood purification by dialysis, for example, without the need for external power sources. In the case of the above-mentioned use of drainage catheters from areas in the body which have been the subject of surgical operation which discharge into sterile vessels in order to facilitate the drainage procedure, these vessels, once they have been filled, can be disconnected from the drainage catheter and can be replaced in a manner which is safe from the point of view of infection. A connection in accordance with the invention is characterized in that the connection halves define a space enclosing the aforementioned device, which space, in a particular relative position of the aforementioned device, or with the connection halves in a relative position separate from the attached position, is so arranged as to communicate with or to constitute a part of the aforementioned flow channels, in which case these are blocked in at least one of the connection halves from the unions, which space, when the aforementioned device has another relative position, or with the connection halves in the attached position, also forms a closed chamber which is separated from the flow channels, and in that present in the wall of the first and/or the second connection half, which defines the aforementioned space, are penetrable membranes via which a fluid preferably with disinfecting properties can be introduced into and removed from the aforementioned space and/or flow channels.

In order to permit the temporary separation of the connection halves for a fairly lengthy period, without the risk of infections, the connection includes, as will be appreciated from a first particular characteristic feature of the invention, a cover in place of the second connection half, which cover lacks unions but has penetrable membranes corresponding to those present on the second connection half, which cover can be applied to the aforementioned first connection half when the flow channels are blocked from the unions, and is itself so arranged as to adopt, or as to permit the device to adopt the relative positions in which the aforementioned space communicates with the flow channels and forms the closed chamber which is separated from the flow channels.

In accordance with a second particular characteristic feature of the invention, the flow channels and the space, with the aforementioned device in the relative position, or with the connection halves in the position in which the space communicates with the flow channels, are connected in series between the membrane, so as to achieve the greatest possible disinfection effect when flushing through with a disinfectant fluid, and as a means of establishing that the flow channels are not blocked.

In view of the fact that, as will be appreciated from a further particular characteristic feature of the invention, with the aforementioned devices or connection halves in the relative position in which the connections are blocked from the aforementioned space and flow channels, these and the space, which is divided by the aforementioned device into two subsidiary spaces which communicate with one another by means of an external line between connections in the second connection half, are connected in series between membranes in the aforementioned first connection half, an opportunity is provided for disinfecting the flow channels, the space and the line and, at the same time, for checking for the presence of any obstructions to the flow.

In accordance with a further particular characteristic feature of the invention the connection comprises a part supported in the second connection half in such a way that it is free to move and is so arranged, with the device in the relative position in which the unions of the connection are blocked, as to be brought into engagement with it in order operatively to actuate it to adopt the aforementioned relative positions.

Since it is intended to be inserted subcutaneously by surgical operation, one half of the connection in accordance with the invention has a collar of biocompatible material intended to be covered by skin growing over it, which collar exhibits a pattern of protrusions, indentations and/or transcurrent holes so arranged as to provide space for blood vessels.

In order to prevent infection of the sealing surfaces of the connection, those surfaces which are effective in blocking the unions in the relative position of the connection halves or the device are so arranged, when in other relative positions, as to define the closed space, in so doing being exposed to the aforementioned fluid.

BRIEF DESCRIPTION OF THE DRAWINGS

Other characteristic features of the invention will be apparent from the following description with reference to the accompanying drawing, in which FIGS. 1a–d illustrate in longitudinal section an embodiment of a connection in accordance with the invention with a union in each half of the connection. FIG. 1a shows the halves of the connection separated from one another; FIG. 1b shows the connection halves attached in a first relative position in which the inside of the connection can be flushed through with a disinfectant fluid. In FIG. 1c the connection halves are shown connected together in a second relative position in which the aforementioned fluid is enclosed inside two annular chambers, and in FIG. 1d the connection is so arranged that the unions communicate with one another. FIG. 2a illustrates in longitudinal section, and FIG. 2b presents half a cross section through two different levels of an embodiment of a connection in accordance with the invention, in which the connection halves each have two unions, one of which halves is intended to be inserted subcutaneously by surgical operation. FIGS. 3a, 3b illustrate in longitudinal section, and FIGS. 3c–3e in cross section a further embodiment of a connection in accordance with the invention, the halves of which each have two unions, and one of which halves is intended to be inserted subcutaneously by surgical operation. FIGS. 3a, 3b show the connection halves separated from one another and attached to one another, and FIGS. 3c–3e illustrate different relative positions of a device supported in the first connection half so that it is free to move, which positions are equivalent to the connection being blocked, shunt-connected, or providing free passage. FIG. 3f illustrates a cover so arranged as to replace one of the connection halves. FIG. 5b illustrates an embodiment of a male component belonging to the embodiment of the connection in accordance with FIG. 5a.

Figure 1B:
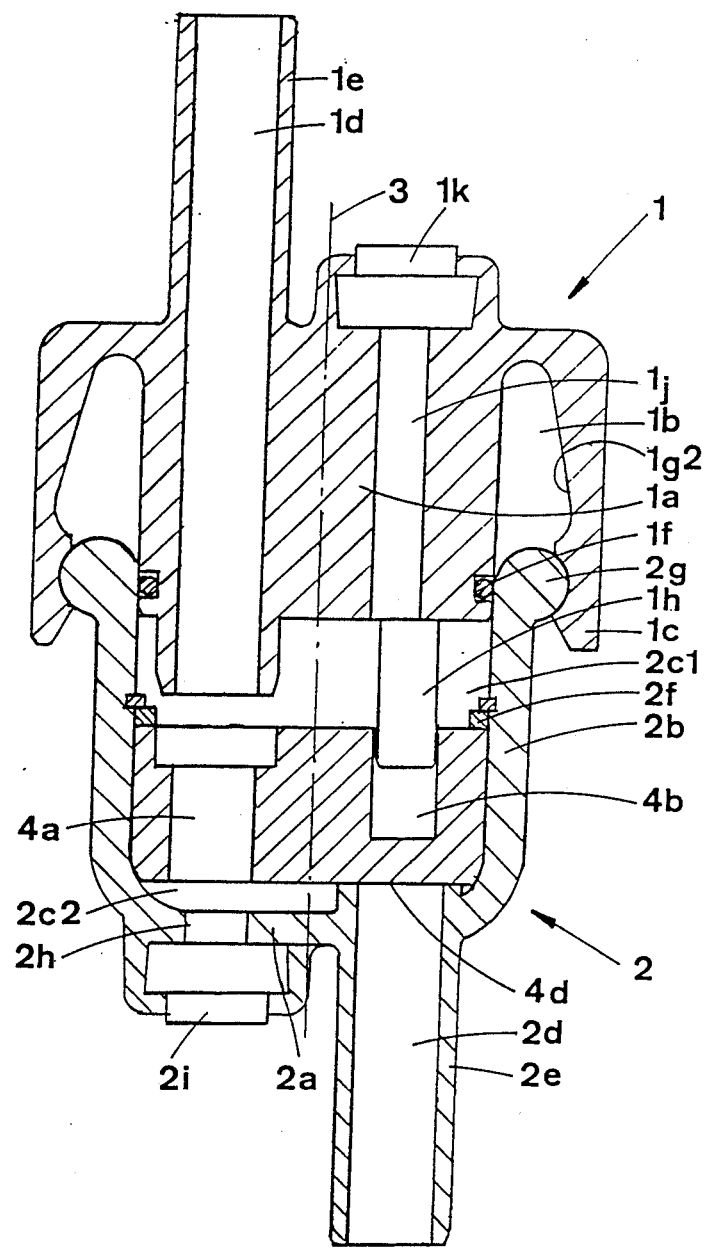

In the following description of the invention components with identical or similar functions have been given the same reference designations.

In FIGS. 1a–1d the designations 1 and 2 are generally used in respect of two connection halves which can be brought together by axial relative movements in order to be joined together and separated from one another. The connection half 2, which can be regarded as a female component, is of cup-shaped design with a bottom 2a and a cylindrical wall 2b which define a space 2c. Connection half 1 constitutes a male component and has a central part 1a which fits into the space 2c of the female component 2 and an annular space 1b arranged around the central part, into which annular space the wall 2b is capable of being introduced and which is defined in the outward sense by a cylindrical wall 1c. When the connection halves 1, 2 are joined together, see FIGS. 1c and 1d, the male component 1 partially encloses the female component 2.

After having been brought together, the connection halves 1, 2 can be rotated relative to one another about an axis of symmetry 3.

The connection halves 1 and 2 each have a transcurrent axial duct 1d and 2d arranged at an identical axial distance from the axis of symmetry 3, and executed on the outsides of the connection halves as pipe unions 1e and 2e. A device 4 is pivotally mounted in the space 2c in the connection half 2, so that it is capable of being rotated about the axis of symmetry 3. The device 4 is is retained in the space 2c by a combination of a locking ring and a compression ring 2f. A sealing ring 1f provides a seal between the central part 1a and the wall 2b. The device 4 is executed with a transcurrent duct 4a, with the help of which, in a distinct relative position between the device 4 and the connection halves 1 and 2, an open flow channel can be provided between the ducts 1d and 2d, but is also so arranged, at least when the halves are separated from one another, as to block the flow channel via the duct 2d. The manner in which this is achieved is described later.

In a connection in accordance with the present invention the connection halves 1, 2 are so arranged as to adopt one of two alternative connection positions. These relative positions can be achieved in many different ways. In the embodiment in accordance with FIGS. 1a–1d the wall 2b of the female component 2 exhibits an outward-facing bead 2g at its outer edge, and the wall 1c of the male component exhibits two corresponding annular grooves, in conjunction with which it is assumed that one or both walls 1c, 2b are sufficiently flexible for the bead 2g to be capable of snapping into engagement in one of the grooves 1g1 and 1g2.

Figure 1C:
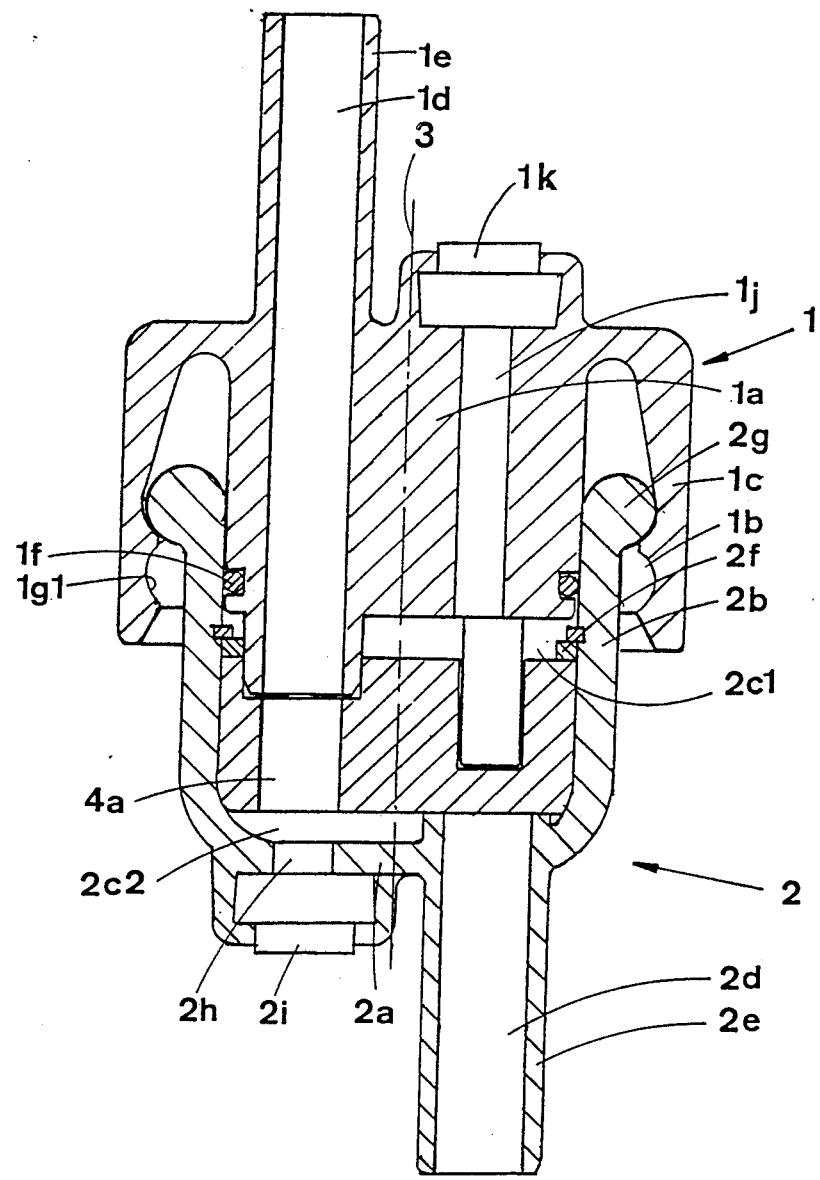

The male component has a driving pin 1h projecting from the central part 1a, which pin is intended to project in both attachment positions into a corresponding hole 4b in the device 4, at the same time as which it is assumed that the ducts 1d and 4a in the inner attachment position, that is to say when the bead 2g is located in the annular groove 1g2, communicate with one another in a fluid-tight manner; see FIG. 1c. This is achieved in the embodiment illustrated in FIGS. 1a–1d in that a tubular prolongation 1i of the duct 1d projects into a corresponding widened part 4c of the duct 4a. Achieved by means of the driving pin 1h are, on the one hand, the joining together of the male component 1 and the device 4 and, on the other hand, the circumstance in which the aforementioned parts can be rotated simultaneously relative to the female component 2 in order respectively to open and block the aforementioned flow channel through the ducts 1d, 4a and 2d. It is also conveniently so arranged, for example with a combination of a guide pin and a guide groove, that the male and female components can be attached to one another and separated from one another only in a relative position between the aforementioned components such that the duct 2d is blocked by a sealing surface 4d on the device 4, which is so arranged as to form a seal against the opening of the aforementioned duct 2d.

Illustrated in FIG. 1b are the connection halves 1, 2 attached to one another in an outer attachment position in which the bead 2g is in engagement with the annular groove 1g1. The connection halves 1, 2 together with the device 4 form a space 2c1, and a space 2c2 is present between the bottom 2a of the female component 2 and the device 4. The spaces 2c1 and 2c2 communicate with one another via the duct 4a. The duct 1d is in connection with the space 2c1, which is itself in connection with a duct 1j, the outer end of which is sealed by means of a penetrable membrane 1k. Present in a similar manner in the female component 2 is a duct 2h which is in connection with the space 2c2, and the outer end of which is sealed by means of a penetrable membrane 2i. A disinfectant fluid can be introduced into the spaces 2c1 and 2c2 and the ducts 1d and 4a by means of a hypodermic syringe via the membranes 1k and 2i, in so doing achieving the disinfection of the walls of the aforementioned spaces and ducts.

In FIG. 1c the connection halves 1, 2 are attached to one another in an inner attachment position. The bead 2g is now in engagement with the annular groove 1g2, and the ducts 1d and 4a communicate with one another and with the space 2c2 in a fluid-tight manner. The volume of the previous space 2c1, which is now separated from the flow channels and forms a closed chamber which communicates with the duct 1j in the male component 1, has now been reduced. It should be noted that the possibility exists for leakage flows to occur between the wall 2b and the wall of the device 4 from the chamber 2c1 into the chamber 2c2 and the duct 2h. In the aforementioned spaces and along the paths of the leakage flows any remaining quantities of the disinfectant fluid will provide protection coating the flow channels, on the one hand against bacteria which may possibly enter via the seal 1f, and on the other hand against bacteria which attempt to make their way from the flow channels to the outside of the connection.

Figure 1D:
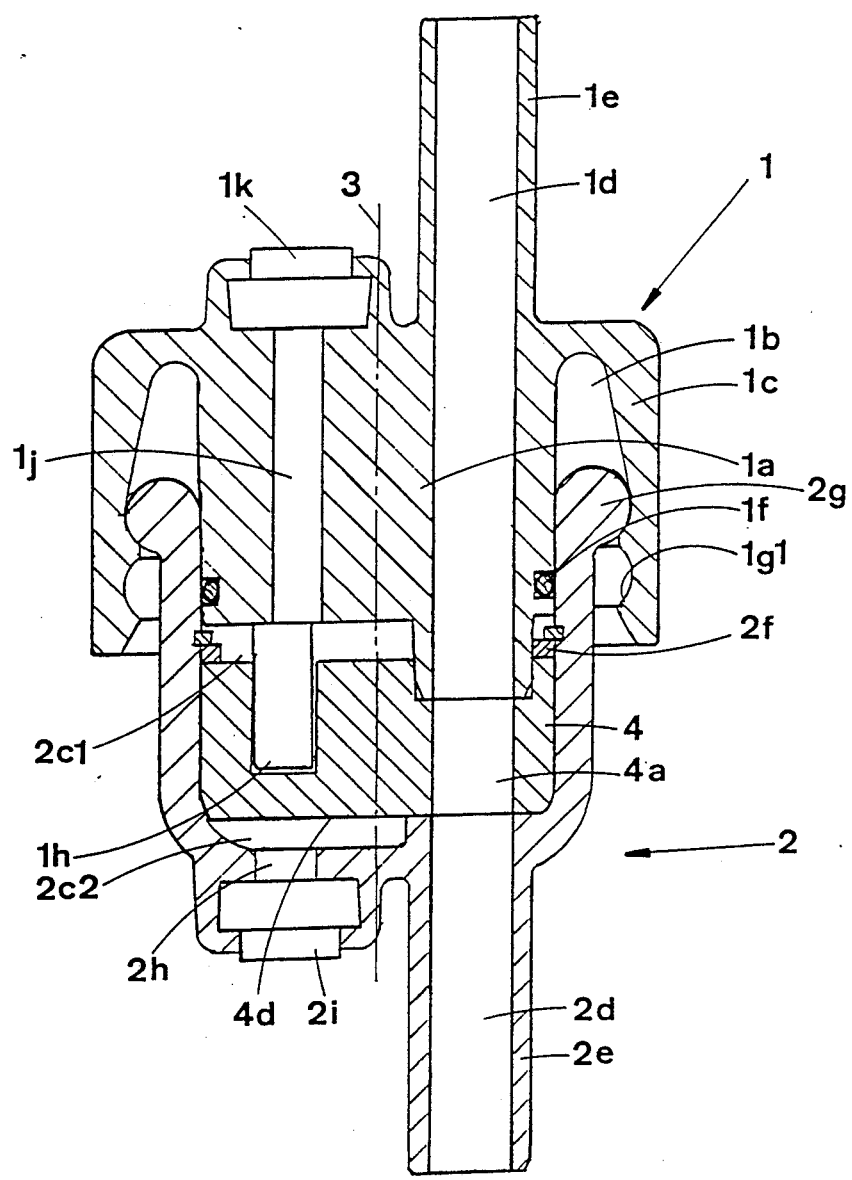

In order to provide an unobstructed flow channel through the ducts 1d, 4a and 2d, the male component 1 and with it the device 4 are now caused to rotate by the engagement of the driving pin 1h in the hole 4b relative to the feamle compnent 2 as far as the position illustrated in FIG. 1d. It must be noted that the sealing surface 4d of the device 4, which previously formed a seal against the opening of the duct 2d, now faces towards the space 2c2 and is thus disinfected by the disinfectant fluid which is present there and can be topped up, if necessary, via the membrane 2i. In a similar manner the space 2c1 can be topped up with disinfectant fluid, if required, via the membrane 1k and the duct 1j. The aforementioned spaces 2c1 and 2c2 filled with a disinfectant fluid thus form an effective infection barrier.

In the embodiment of a connection in accordance with the invention illustrated in FIGS. 2a and 2b, the female component, which has two unions 2e1 and 2e2 with associated ducts 2d1 and 2d2, is intended to be inserted subcutaneously by surgical operation, in conjunction with which the unions are connected to veins or arteries or to other vessels for body fluids. In order to provide a good passage through the skin, the female component 2 is executed with a collar 5 made of a biocompatible material and intended to be covered by skin 6 growing over it. In order to provide space for the blood vessels of the skin, the collar 5 is executed with transcurrent holes, protrusions and indentations, as indicated in FIG. 2b. The male component 1, too, has two unions 1e1 and 1e2 with associated ducts 1d1 and 1d2. This embodiment also has an outer and an inner attachment position for the male and female components 1, 2, in which the bead 2g is in engagement with the annular grooves 1g1 and 1g2.

In the outer attachment position illustrated in FIG. 2a the ducts 2d1 and 2d2 communicate with one another via a duct in the device 4 in a similar manner to that in the embodiment described above. The opportunity is provided via the membrane 1k and the duct 1j, which constitute a part of the duct 1d1, for the introduction of, for example, a disinfectant fluid into the space 2c1, which communicates with the ducts 1d1 and 1d2, see FIG. 2b. This means that the last-mentioned space and ducts can be disinfected in a simple manner.

In the inner attachment position the space 2c1 has been given a volume which is reduced relative to its previous volume and constitutes an entirely separate chamber. The disinfectant fluid which is present inside the chamber forms an infection barrier, as in the previously described embodiment. As in the previous embodiment the device 4 can be caused by means of the driving pin at different rotational positions to provide two different flow situations. In a first rotatiorial position the ducts 2d1 and 2d2 communicate, whilst the ducts 1d1 and 1d2 are blocked. In a second rotational position the ducts 2d1 and 1d1, and 2d2 and 1d2 respectively communicate with one another. This rotational position is used when it is wished to connect an external arrangement, for instance a pump or a filter, into a blood vessel, for example.

The connections described in relation to FIGS. 1a–1d and 2a, 2b share the common feature that the space 2c1 is defined by an axial relative movement between the connection halves 1, 2, such that the space forms a closed chamber which is isolated from the flow channels.

Described below with reference to FIGS. 3a–3f is an embodiment of a connection in accordance with the invention, in which the abovementioned isolation of the space is achieved by relative rotation of, on the one hand, the male component 1 and the device 4 and, on the other hand, the female component 2. The connection half 2 is intended to be inserted by surgery and is provided with a collar 5 for this purpose. The male component has two unions 1e1, 1e2, with associated ducts 1d1, 1d2 which gently bend outwards towards the generated surface of the central part 1a of the male component. Operative connection between the male component 1 and the device 4 is achieved through an appropriate combination of axial grooves 1m and corresponding projections 4e, for example in the manner illustrated in FIGS. 3c–3e. The male component exhibits at the bottom a groove 1l so arranged as to be in connection with an adjacent flow channel 4f (by-pass) through the device 4 when the connection halves are attached to one another in the manner illustrated in FIG. 3b. Also indicated in this Figure is an annular chamber 8, which is defined by parts of the walls of the male and female components 1, 2 situated between the sealing ring 1f and a sealing ring 2j. This chamber is intended to be filled with a disinfectant fluid so as to form a barrier against bacteria passing to and from the flow channels, in a similar manner to that which is applicable in the previously described embodiments of the connection in accordance with the invention. Filling of the chamber 8 takes place independently through a change in displacement in conjunction with the introduction of the male component 1 into the female component 2.

The three different flow alternatives of the connection are now explained with reference to FIGS. 3c–3e, in conjunction with which the rotational position between the male component. 1 and the female component 2 and the device 4 are of critical significance. In FIG. 3c the ducts 1d1 and 1d2 communicate with one another via the chambers 2c between the wall 2b of the female component and the device 4, the flow channel 4f and the groove 11. The ducts 2d1 and 2d2 are blocked by means of sealing surfaces 4a1 and 4a2, which are in sealing contact against the openings of the aforementioned ducts into the chamber. This rotational position is temporary and is used, for example, when it is wished to flush through all the flow channels by connecting these in series, without in so doing affecting the blood vessels 2d1 and 2d2 attached to the surgically inserted female component.

Figure 3D:
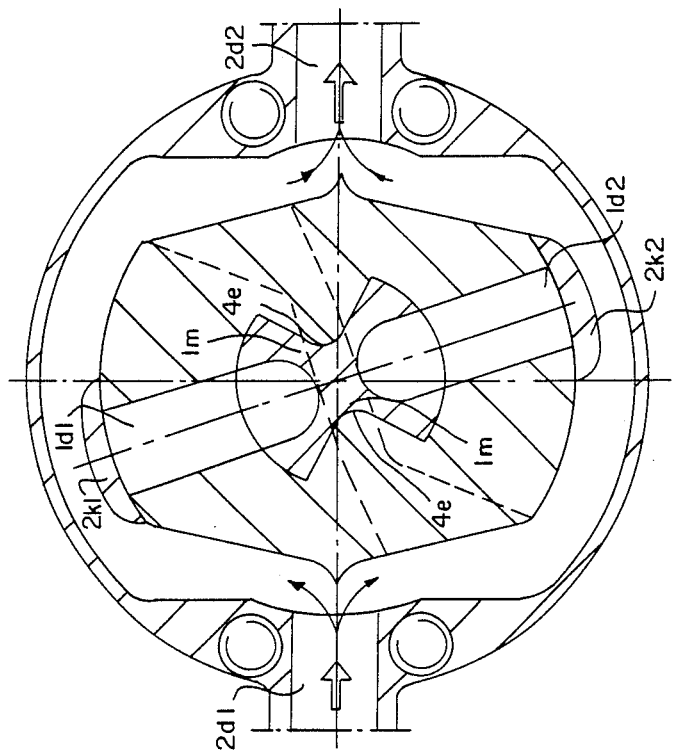
Figure 3C:
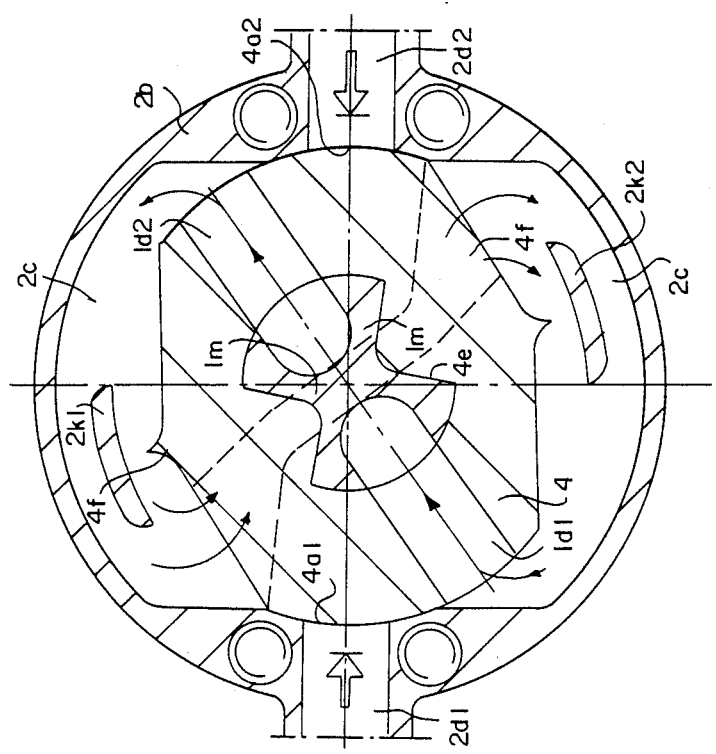

The rotational position in accordance with FIG. 3d means that the ducts 1d1 and 1d2 are blocked by sealing devices 2k1, 2k2 which are securely attached to the bottom 2a of the female component 2 and make sealing contact with the sealing surfaces 4a1, 4a2 of the device 4. The ducts 2d1 and 2d2 communicate with one another via the chamber 2c. The rotational position in accordance with FIG. 3d is a by-pass position in which the connection has to all intents and purposes no effect on the flow in the attached blood vessels. In the rotational position illustrated in FIG. 3e the ducts 1d1 and 2d1, and 1d2 and 2d2 respectively communicate with one another. This rotational position is the one used most commonly with the connection, and means that the opportunity is provided for connecting a pump or filter, for example, via the unions 1e1, 1e2 which correspond to the ducts 1d1, 1d2.

The embodiment of a connection in accordance with the invention described above also comprises a cover 7 intended under certain conditions to replace the male component 1. The cover 7 has no unions, but has a penetrable membrane 7a and a duct 7b, similar to 11, and a by-pass duct 7c running across it, similar to the by-pass duct 11 of the male component. A precondition if the cover 7 is to be capable of being fitted in place of the male component or of being removed is that the ducts 2d1 and 2d2 must be blocked by the device 4, that is to say the latter must exhibit the angular position illustrated in FIG. 3c.

Figure 3G:
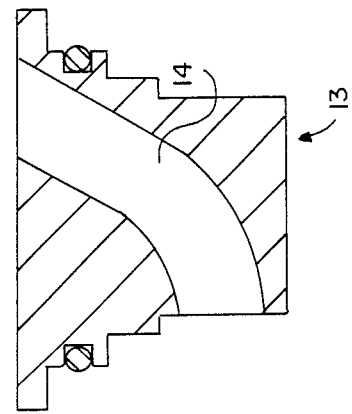
FIG. 3g illustrates a detail, rather like the cover in accordance with FIG. 3f, but executed with a central, curved channel.

As an alternative to the cover 7 it is possible, under the same conditions as are applicable to it, to introduce a component part 13, see FIG. 3g, with a central, curved duct 14, which, by causing the component 13 to rotate, can be caused to communicate alternately with the ducts 2d1, 2d2. By using an appropriate tool, the opportunity is thus provided for performing cleaning of the ducts 2d1, 2d2 via the duct 14.

Figure 4:
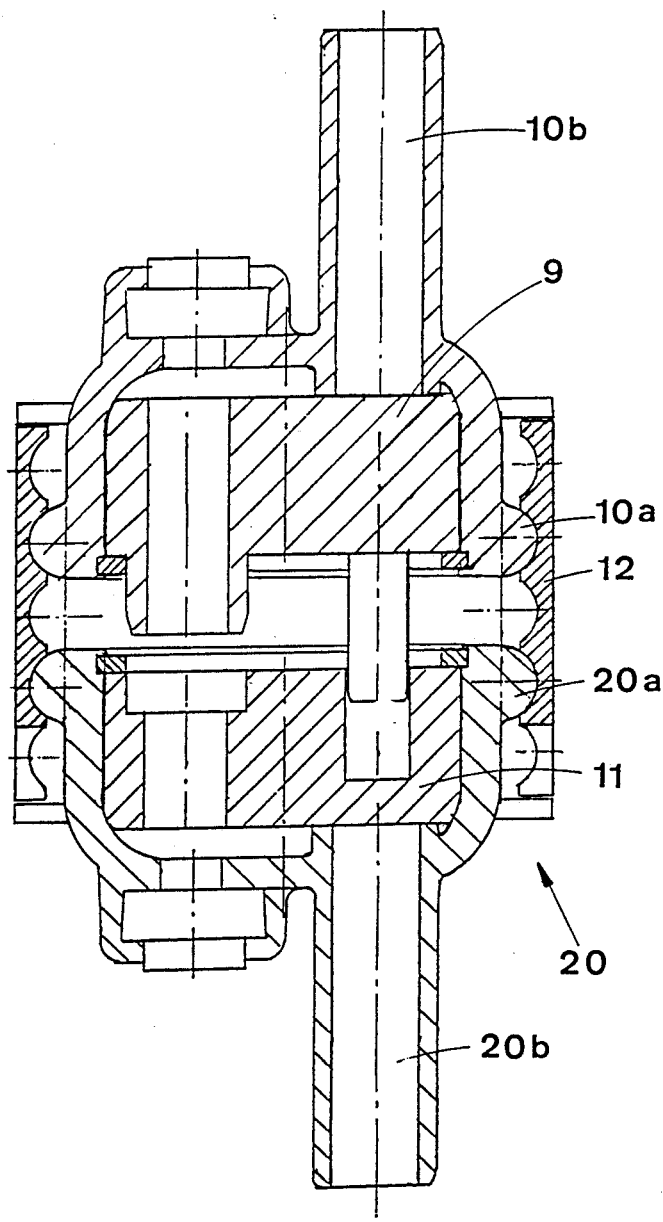
FIG. 4 illustrates in longitudinal section an alternative embodiment of a connection in accordance with the present invention, which has essentially identically executed closable connection halves, that is to say they are capable of being closed and are not distinctly male and female components.

In the embodiment of the connection in accordance with the invention illustrated in FIG. 4, both connection halves 10, 20 are much the same as the female component 2 in accordance with FIGS. 1a, 1d, that it to say they both have a pivotally mounted device 9 and 10 essentially identical with the device 4 in accordance with FIG. 1a. The connection halves 10, 20 are both executed with a bead 10a, 20a so arranged as to be in engagement with corresponding grooves in a locking device 11. Other component parts of the connection in accordance with FIG. 4, such as membranes, flow ducts, driving pins, and locking rings, are similar to those in the embodiment in accordance with FIGS. 1a–1d. What is achieved by this embodiment over and above the embodiment in accordance with FIGS. 1a–1d is that both ducts 10b, 20b can be blocked by means of the respective device 9, 10 when the connection halves are separated from one another.

Figure 5B:
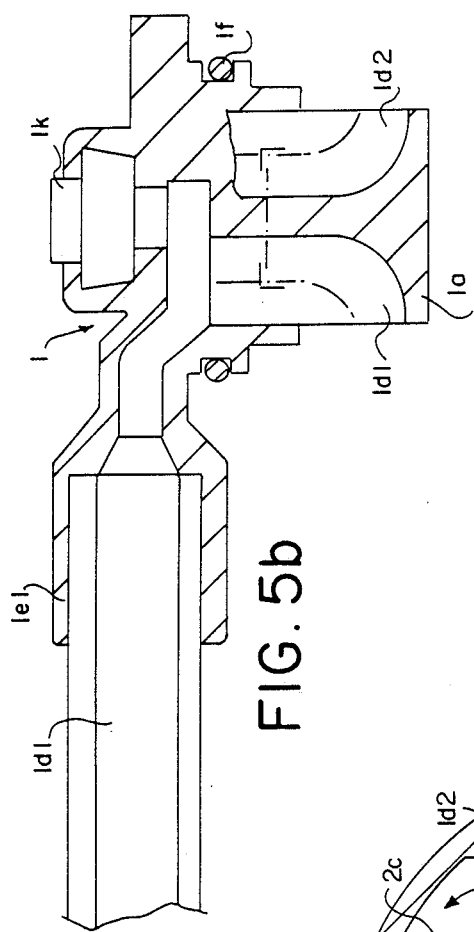
Figure 5A:
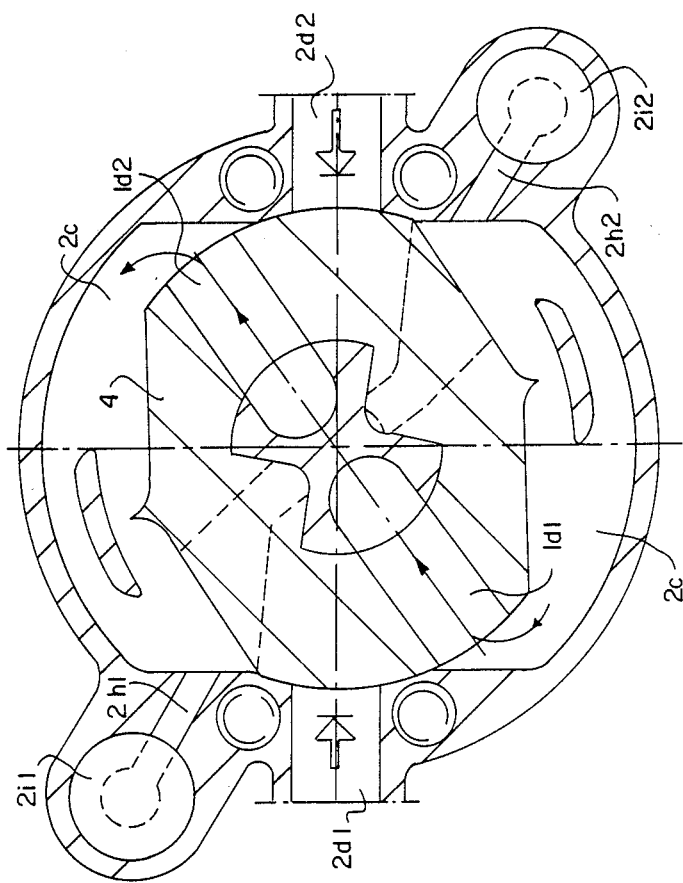
FIG. 5a illustrates in a section similar to that in accordance with FIG. 3c an alternative embodiment of a connection in accordance with the invention, that half of which, which is capable of being inserted by surgical operation, is executed with two membranes which are capable of being penetrated by a cannula.

The embodiment of a connection in accordance with the invention illustrated in FIG. 5a differs from the embodiment previously described in conjunction with FIGS. 3a–3e primarily in that the male component in the first-mentioned embodiment has two penetrable membranes 2i1, 2i2, which are arranged close to the connections 2d1 and 2d2 and which communicate via ducts 2h1 and 2h2 with the space 2c. If a comparison is made with the male component 1 in accordance with FIG. 3a, which has a by-pass duct 11, it will be noted that the male component 1 in accordance with FIG. 5a lacks this duct. In the position of the device 4 illustrated in FIG. 5a, in which it blocks the flow channels 2d1, 2d2, this embodiment means that there is provided via an external line (not shown) attached to the connections 1c1, 1c2 between the membranes 2i1, 2i2 a series-connected flow channel consisting of the ducts 2h1, 2h2, the space 2, the flow channels 1d1, 1d2 and the aforementioned line. It is thus possible, by injecting a disinfectant fluid through one of the membranes and by sucking it out through the other membrane, to achieve the disinfection of the entire series-connected flow channel. Ventilation and the ability to verify that the flow channel is intact are also permitted at the same time. It is obvious that the aforementioned line can contain, for example, a filter which is capable conveniently of being connected and disconnected by means of a connection in accordance with FIGS. 1a–1d, in this way achieving the advantages indicated in conjunction with the aforementioned Figures.

I claim:

1. Connection, especially for medical applications, comprising two connection halves (1, 2) each having at least one union (1e, 2e) and a device (4) supported in a first connection half (2) so that it is free to move, said device being so arranged, when in distinct positions relative to the aforementioned first connection half (2), as to open flow channels (1d, 4a, 2d) between the unions (1e, 2e) when the halves (1, 2) are attached to one another, and to block the flow channels (1d, 4a, 2d) at least when the halves (1, 2) are separated from one another, characterized in that the connection halves (1, 2) define a space (2c1) enclosing the device (4), which space, in a particular relative position of the aforementioned device (4), or with the connection halves (1, 2) in a relative position separate from the attached position, is so arranged as to communicate with or as to constitute a part of the aforementioned flow channels (1d, 4a, 2d), in which case these are blocked in at least one of the connection halves from the unions (1e, 2e), which space, when the device (4) has another relative position, or with the connection halves (1, 2) in the attached position, also forms a closed chamber which is separated from the flow channels (1d, 4a, 2d), and in that present in one part of the wall of the second connection half (1), which defines the aforementioned space (2c1), are penetrable membranes (1k; 2i) via which a fluid preferably with disinfectant properties can be introduced into and removed from same when the space (2c1) communicates with the flow channels (1d, 4a, 2d).

2. Connection according to Patent claim 1, characterized in that it comprises a cover (7) in place of the second connection half (1), which cover lacks unions but has penetrable membranes (7a) corresponding to those which are present on the second connection half (1), which cover (7) can be applied to the aforementioned first connection half (2) when the flow channels are blocked from the unions, and is itself so arranged as to adopt, or as to permit the device (4) to adopt the relative positions in which the aforementioned space (2c1) communicates with the flow channels and forms the closed chamber which is separated from the flow channels.

3. Connection according to Patent claim 1, characterized in that each connection half (1, 2) has a pair of unions (1e1, 1e2, 2e1, 2e2), in that the aforementioned device (4) has three distinct relative positions, one of which involves the flow channels communicating with the aforementioned space (2c1) at the same time as the unions are blocked, a second involves each union on one of the connection halves communicating with a corresponding union on the other half at the same time as the closed chamber (2c1) is established, and the third involves the aforementioned chamber (2c1) being established, and in that the unions of the aforementioned first connection half communicate with one another.

4. Connection according to Patent claim 1, characterized in that the connection halves (1, 2) each have a pair of unions (1e1, 1e2; 2e1, 2e2) and, when attached to one another, have two distinct relative positions, in one of which the flow channels communicate with the aforementioned space (2c1) at the same time as the unions are blocked, and in the other the closed chamber (2c1) is established, and the aforementioned device (4) is so arranged, when in a first position, as to provide flow channels between the respective union on one connection half and the corresponding union on the second half and, when in a second position, as to cause the unions on the aforementioned first connection half to communicate with one another.

5. Connection according to Patent claim 1, characterized in that, in the relative position of the aforementioned device (4) or of the connection halves (1, 2) in which the connections are blocked from the aforementioned space (2c) and flow channels, these and the space (2c) are connected in series between membranes (1k; 2i) arranged in the second connection half (1) via ducts (4f, 1l) in the device (4) and the second connection half (1).

6. Connection according to Patent claim 1, characterized in that, in the relative position of the aforementioned device (4) or connection halves (1, 2) in which the connections are blocked from the aforementioned space and flow channels, these and the space, which is divided by the aforementioned device (4) into two subsidiary spaces, which, by means of an external line between the connections (1e1, 1e2) in the second connection half (1), communicate with one another, are connected in series between membranes (2i1, 2i2) in the aforementioned first connection half (2).

7. Connection according to Patent claim 1, characterized in that it comprises a part supported in the second connection half (1) in such a way that it is free to move and so arranged, in the relative position of the device (4) in which the unions of the connnection are blocked, as to be brought into engagement with it in order operatively to actuate it to adopt the aforementioned relative positions.

8. Connection according to any of the preceding Patent claims, characterized in that one half (2) is intended to be inserted subcutaneously by surgical operation and has a collar (5) of biocompatible material intended to be covered by skin (6) growing over it, which collar (5) exhibits a pattern of protrusions, indentations and transcurrent holes so arranged as to provide space for blood vessels.

9. Connection according to Patent claim 1, characterized in that, of the sealing surfaces of the connection, those which are effective in blocking the unions in a relative position intended for this purpose of the connection halves (1, 2) or the device (4) are so arranged, when in other relative positions, as to define the closed space, in so doing being exposed to the aforementioned fluid.

* * * * *